United States Patent

Klaus et al.

[11] Patent Number: 5,958,956
[45] Date of Patent: Sep. 28, 1999

[54] AROMATIC CARBOXYLIC ACID ESTERS

[75] Inventors: Michael Klaus, Weil am Rhein, Germany; Peter Mohr, Basel, Switzerland

[73] Assignee: Hoffmann-La Roche Inc., Nutley, N.J.

[21] Appl. No.: 09/007,613

[22] Filed: Jan. 15, 1998

Related U.S. Application Data

[62] Division of application No. 08/735,941, Oct. 23, 1996, Pat. No. 5,726,191.

[30] Foreign Application Priority Data

Nov. 16, 1995 [CH] Switzerland .................... 3249/95

[51] Int. Cl.$^6$ ................... A61K 31/44; C07D 213/63; C07D 213/70
[52] U.S. Cl. ............................. 514/350; 546/298
[58] Field of Search .............. 514/350; 546/298

[56] References Cited

U.S. PATENT DOCUMENTS

| | | | |
|---|---|---|---|
| 4,535,086 | 8/1985 | Klaus et al. ............... | 514/337 |
| 4,703,110 | 10/1987 | Shudo .................... | 534/566 |
| 5,468,897 | 11/1995 | Shroot et al. ............. | 560/18 |

FOREIGN PATENT DOCUMENTS

| | | |
|---|---|---|
| 0 409 728 | 7/1990 | European Pat. Off. . |
| 0617020 | 9/1994 | European Pat. Off. . |
| WO 9306086 | 4/1993 | WIPO . |
| WO 94/15902 | 7/1994 | WIPO . |

OTHER PUBLICATIONS

Science 237: pp. 1333–1336 (1987).
J. Pathol. 129: pp. 601–613 (1987).
J. Org. Chem. 49, pp. 4092–4094 (1984).

Primary Examiner—Alan L. Rotman
Attorney, Agent, or Firm—George W. Johnston; Patricia S. Rocha-Tramaloni; Robert A. Silverman

[57] ABSTRACT

A compound of the formula

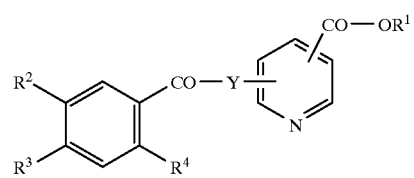

wherein $R^1$ is hydrogen or $C_{1-6}$-alkyl;

$R^2$ is $C_{1-6}$-alkyl or adamantyl;

$R^3$ is $C_{1-6}$-alkyl or hydroxy; or $R^2$ and $R^3$ taken together are —$(CR^6R^7)_n$—;

$R^4$ is $C_{2-8}$-alkyl, $C_{2-8}$-alkenyl, $C_{2-8}$-alkynyl, —$OCH_2R^5$ or $C_{2-8}$-alkanoyl; and hydrogen when $R^3$ is hydroxy;

$R^5$ is $C_{1-6}$-alkyl, $C_{2-6}$-alkenyl or $C_{2-6}$-alkynyl;

$R^6$ and $R^7$ are hydrogen or $C_{1-6}$-alkyl;

Y is oxygen or sulphur; and n is 3, 4 or 5, and pharmaceutically usable salts of carboxylic acids of formula I act as selective ligands of retinoic acid γ-receptors and are useful for the treatment of epithelial lesions.

2 Claims, No Drawings

AROMATIC CARBOXYLIC ACID ESTERS

This is a division of application Ser. No. 08/735,941, filed Oct. 23, 1996 now U.S. Pat. No. 5,726,191.

BRIEF SUMMARY OF THE INVENTION

The present invention relates to aromatic carboxylic acid esters, their manufacture and use as medicaments. In particular, the invention relates to compounds of the formula

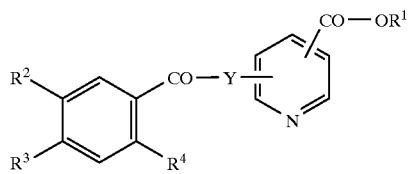

wherein
- $R^1$ is hydrogen or $C_{1-6}$-alkyl;
- $R^2$ is $C_{1-6}$-alkyl or adamantyl;
- $R^3$ is $C_{1-6}$-alkyl or hydroxy; or
- $R^2$ and $R^3$ taken together are $-(CR^6R^7)_n-$;
- $R^4$ is $C_{2-8}$-alkyl, $C_{2-8}$-alkenyl, $C_{2-8}$-alkynyl, $-OCH_2R^5$ or $C_{2-8}$-alkanoyl; and hydrogen when $R^3$ is hydroxy;
- $R^5$ is $C_{1-6}$-alkyl, $C_{2-6}$-alkenyl or $C_{2-6}$-alkynyl;
- $R^6$ and $R^7$ are hydrogen or $C_{1-6}$-alkyl;
- Y is oxygen or sulphur; and
- n is 3, 4 or 5, and pharmaceutically usable salts of carboxylic acids of formula I.

DETAILED DESCRIPTION OF THE INVENTION

The present invention relates to aromatic carboxylic acid esters, their manufacture and use as medicaments. In particular, the invention relates to esters of aromatic carboxylic acids with hydroxy- or mercapto-pyridinecarboxylic acids and acid esters of the formula

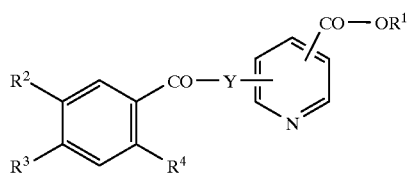

wherein
- $R^1$ is hydrogen or $C_{1-6}$-alkyl;
- $R^2$ is $C_{1-6}$-alkyl or adamantyl;
- $R^3$ is $C_{1-6}$-alkyl or hydroxy; or
- $R^2$ and $R^3$ taken together are $-(CR^6R^7)_n-$;
- $R^4$ is $C_{2-8}$-alkyl, $C_{2-8}$-alkenyl, $C_{2-8}$-alkynyl, $-OCH_2R^5$ or $C_{2-8}$-alkanoyl; and hydrogen when $R^3$ is hydroxy;
- $R^5$ is $C_{1-6}$-alkyl, $C_{2-6}$-alkenyl or $C_{2-6}$-alkynyl;
- $R^6$ and $R^7$ are hydrogen or $C_{1-6}$-alkyl;
- Y is oxygen or sulphur; and
- n is 3, 4 or 5, and pharmaceutically usable salts of carboxylic acids of formula I.

Furthermore, the invention is concerned with pharmaceutical preparations based on compounds of formula I or their salts, a process for the manufacture of compounds of formula I and the use of compounds of formula I as medicaments and as active substances in the production of medicaments.

The notations "$C_{1-6}$", "$C_{2-6}$", and "$C_{2-8}$" used herein stand for groups with 1–6, 2–6 and 2–8 carbon atoms, respectively. Alkyl residues can be straight-chain or branched. The alkyl residues $R^1$ are preferably straight-chain such as methyl, ethyl, propyl, butyl, pentyl and hexyl. Alkyl residues $R^2$ and $R^3$ are preferably branched alkyl residues such as tert.-butyl. Alkyl residues $R^4$ and $R^5$ are preferably straight-chain such as ethyl, propyl, butyl, pentyl, hexyl, heptyl and octyl. Examples of alkenyl residues are preferably straight-chain alkenyl residues such as vinyl, 1- and 2-propenyl, and 2-butenyl. Ethynyl, 1- and 2-propynyl and 1- and 2-butynyl are examples of alkynyl residues. Examples of $C_{2-8}$-alkanoyl residues are preferably straight-chain alkanoyl residues such as acetyl, propionyl, butyryl, pentanoyl, hexanoyl, heptanoyl and octanoyl.

In a preferred embodiment of the invention the pyridinecarboxylic acid residue in the compounds of formula I is a nicotinic acid residue, that is, when $R^1$ is hydrogen, especially a nicotinic acid residue linked in the 6-position. Furthermore, compounds of formula I in which Y is oxygen are preferred as well as those in which $R^2$ and $R^3$ together represent $-(CR^6R^7)_n-$ and $R^6$ and $R^7$ represent hydrogen or methyl, especially preferred are compounds of formula I in which $R^2$ and $R^3$ together represent a residue $-C(CH_3)_2CH_2CH_2C(CH_3)_2-$, $-C(CH_3)_2(CH_2)_4-$ or $-C(CH_3)_2(CH_2)_2-$. $R^4$ is preferably pentyl, hexyl, 1E-hexenyl, hexanoyl or butoxy.

Examples of preferred compounds of formula I are
6-(3-hexyl-5,5,8,8-tetramethyl-5,6,7,8-tetrahydro-naphthalen-2-yl-carbonyloxy)-nicotinic acid,
6-(3-pentyl-5,5,8,8-tetramethyl-5,6,7,8-tetrahydro-naphthalen-2-yl-carbonyloxy)-nicotinic acid,
6-(3-hexyl-5,5-dimethyl-6,7,8,9-tetrahydro-5H-benzocyclohepten-2-yl-carbonyloxy)-nicotinic acid,
6-(3-hex-1-enyl-5,5,8,8-tetramethyl-5,6,7,8-tetrahydro-naphthalen-2-yl-carbonyloxy)-nicotinic acid,
6-(6-hexyl-3,3-dimethyl-indan-5-yl-carbonyloxy)-nicotinic acid,
6-(3-butoxy-5,5,8,8-tetramethyl-5,6,7,8-tetrahydro-naphthalen-2-yl-carbonyloxy)-nicotinic acid,
6-(3-adamantan-1-yl-4-hydroxy-benzoyloxy)-nicotinic acid,
6-(3-hexanoyl-5,5,8,8-tetramethyl-5,6,7,8-tetrahydro-naphthalen-2-yl-carbonyloxy)-nicotinic acid and
6-(3-hexyl-5,5,8,8-tetramethyl-5,6,7,8-tetrahydro-naphthalen-2-yl-carbonylsulphanyl)-nicotinic acid.

The compounds of formula I can be manufactured in accordance with the invention by reacting a compound of formula II

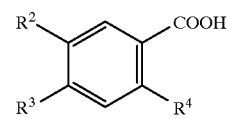

wherein $R^2$, $R^3$ and $R^4$ have the significance given above and a hydroxy group $R^3$ or an oxo group contained in $R^4$ is present in protected form,
with a compound of formula III

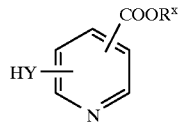

wherein $R^x$ represents a protecting group and Y has the significance given above.

The esterification of the compound of formula II with a compound of formula III can be carried out using known methods. Conveniently, the esterification is effected in the presence of a condensation agent such as dicyclohexylcarbodiimide/dimethyl-aminopyridine in a suitable organic solvent, for example, a halogenated hydrocarbon such as methylene chloride. Examples of protecting groups $R^x$ in compounds of formula III and on a hydroxy group $R^3$ which may be present in compounds of formula II are protecting groups which are cleavable hydrogenolytically, by a transition metal catalysis (for example, $Pd^{(O)}$), or by treatment with $F^-$ ions, such as benzyl, allyl, trimethylsilylethyl or 4-trimethylsilyl-(E)-but-2-enyl. Examples of oxo protecting groups are especially ketal groups such as ethylenedioxy. The introduction and cleavage of such protecting groups can be effected in a known manner.

Examples of salts into which the carboxylic acids of formula I can be converted are alkali metal salts such as Na and K salts, alkaline earth metal salts such as Ca and Mg salts and ammonium salts, for example, salts with alkylamines and hydroxyalkylamines or with other organic bases such as dimethylamine, diethanolamine and piperidine.

The compounds of formulas II and III which are used as starting materials, insofar as they are not known or are described hereinafter, can be prepared in analogy to known procedures or to the procedures described hereinafter.

The compounds in accordance with the invention act as selective ligands of retinoic acid γ-receptors (RAR-γ). They can be used for the therapy and prophylaxis of light- and age-damaged skin, as well as, for the promotion of wound healing, for example of incised wounds, such as surgical wounds, wounds caused by burns and other wounds caused by cutaneous trauma. The suitability of the compounds in accordance with the invention for this purpose can be demonstrated in the models described in Science 237: 1333–1336 (1987) and J. Pathol. 129: 601–613 (1987). Furthermore, the compounds in accordance with the invention can be used for the therapy and prophylaxis of dermatological disorders which are accompanied by epithelial lesions, for example, acne and psoriasis, as well as malignant and premalignant epithelial lesions, tumors and precancerous changes to the mucous membrane in the mouth, tongue, larynx, esophagus, bladder, cervix and colon. The compounds of formula I are distinguished by a low skin-irritating effect and a low teratogenic potential.

The compounds of formula I and their salts can accordingly be used in the form of pharmaceutical preparations.

The preparations for systemic use can be produced, for example, by adding a compound of formula I or a salt thereof as the active ingredient to non-toxic, inert solid or liquid carriers which are usual in such preparations.

The preparations can be administered enterally, parenterally or topically. Preparations in the form of tablets, capsules, dragees, syrups, suspensions, solutions and suppositories are, for example, suitable for enteral administration. Preparations in the form of infusion or injection solutions are suitable for parenteral administration.

For enteral and parenteral administration the compounds of formula I can be administered to adults in amounts of about 1–100 mg, preferably 5–30 mg/day.

For topical use the active substances are conveniently used in the form of ointments, tinctures, creams, solutions, lotions, sprays, suspensions and the like. Ointments and creams as well as solutions are preferred. These preparations designed for topical use can be produced by mixing the process products as active ingredients with non-toxic, inert solid or liquid carriers which are suitable for topical treatment and which are usual in such preparations.

For topical use there are conveniently suitable about 0.001–1%, preferably 0.3–2%, solutions, as well as, about 0.001–1%, preferably 0.01–1%, ointments or creams.

If desired, an antioxidant, for example, tocopherol, N-methyl-γ-tocopheramine, as well as, butylated hydroxyanisole or butylated hydroxytoluene, can be admixed with the preparations.

The efficacy of the compounds in accordance with the invention in the treatment of light-damaged skin will be evident from the experimental procedures described hereinafter:

Elimination of UV-B-Caused Skin Damage in the Hairless Mouse

Hairless mice (HRS/J strain, Jackson Labs, aged 5–7 weeks at the beginning of the experiment) were irradiated three times a week with an arrangement of 8 Westinghouse irradiation lamps (FS40) which were placed about 20 cm above the animals. The radiation dose was controlled by a commerical phototherapeutic control device. The UV-B dose was chosen such that the dosage scarcely exceeded 0.06 $J/cm^2$ and caused a minimal erythema, but no burning or scarring. After a total dose of about 3.5 $J/cm^2$, there resulted a significance elastosis which was evident from a histological report and which was confirmed by measuring the elastane using a radioimmunoassay for desmosin in the total skin. The desmosin content increased two- to three-fold after 3.5 $J/cm^2$ UV-B irradiation. In order to make good the skin damage, the UV irradiation was interrupted and groups of animals were treated separately three times a week with different doses of compounds of formula I dissolved in acetone. These solutions were prepared freshly each week such that the dosage to be administered was present in 100 ml of acetone and was applied topically to an area of about 10 $cm^2$ on the backs of the animals. A control group was treated only with acetone.

After treatment for 10 weeks the animals were killed, skin preparations were prepared and the extent of the recovery was measured quantitatively by Luna staining of the elastin and Van Gieson staining of the collagen. An activity scale was drawn up on this basis with an evaluation of 0 (inactive) to 4 (complete, overall recovery). In this experimental model all-trans-retinoic acid and 13-cis-retinoic acid showed an activity of 2, whereas the tested compounds of formula I showed an activity of 4.

The invention is illustrated in more detail by the following Examples:

EXAMPLE 1

6 g of 3-hexyl-5,5,8,8-tetramethyl-5,6,7,8-tetrahydro-naphthalen-2-yl-carboxylic acid were dissolved in 180 ml of methylene chloride. After the addition of a solution of 4.8 g of benzyl 6-hydroxy-nicotinate in 160 ml of methylene chloride and of 2.3 g of 4-dimethylaminopyridine, the solution was cooled to 0° C. and treated with 4.4 g of dicyclohexylcarbodiimide. The reaction mixture was stirred at 0° C. for 1 hour and at room temperature for 2 hours, thereafter poured into ice-cold aqueous ammonium chloride solution, extracted several times with ether, washed with water, dried over sodium sulfate and evaporated. The crude product, for the most part crystalline, was filtered over silica gel (eluent hexane/ethyl acetate=9:1) and recrystallized from hexane. After repeated crystallization of the mother liquor there were obtained alltogether 5.7 g of benzyl 6-(3-hexyl-5,5,8,8-tetramethyl-5,6,7,8-tetrahydro-naphthalen-2-yl-carbonyloxy)-nicotinate in colorless crystals, m.p. 94–95° C.

This benzyl ester (5.7 g) was dissolved in 450 ml of ethyl acetate and, after the addition of 2.2 g of 10% palladium-charcoal, hydrogenated with hydrogen under normal pressure at room temperature. After 40 min., the hydrogenation was interrupted, the catalyst was filtered off, the filtrate was evaporated and the dark brownish residue was recrystallized from ethyl acetate/hexane. There were obtained 2.8 g of 6-(3-hexyl-5,5,8,8-tetramethyl-5,6,7,8-tetrahydro-naphthalen-2-yl-carbonyloxy)-nicotinic acid in colorless crystals, m.p. 146–149° C. (dec.).

The carboxylic acid used as the starting material was prepared as follows:

15 g of 6-bromo-7-hexyl-1,1,4,4-tetramethyl-1 2,3,4-tetrahydro-naphthalene were dissolved in 180 ml of tetrahydro-furan and treated dropwise at −78° C. with 64.5 ml of a 1.5 molar solution of tert.butyl-lithium in pentane. After stirring at −78° C. for 1 hour, a carbon dioxide stream was conducted vigorously into the reaction vessel for 2 hours. Subsequently, the reaction mixture was acidified by the addition of 190 ml of 2N hydrochloric acid, extracted several times with ethyl acetate, washed with water, dried over sodium sulfate and evaporated. The oily crude product was filtered over silica gel (eluent hexane, then hexane/ethyl acetate=4:1) and recrystallized from hexane. There were obtained 7.6 g of 3-hexyl-5,5,8,8-tetramethyl-5,6,7,8-tetrahydro-naphthalen-2-yl-carboxylic acid in colorless crystals, m.p. 98–99° C.

The benzyl 6-hydroxy-nicotinate used as the starting material was prepared as follows:

30 g of 6-hydroxynicotinic acid were treated with 500 ml of benzyl alcohol and 1 ml of concentrated sulfuric acid. After boiling at reflux for 3 days, the reaction mixture was poured on to ice-water, extracted several times with ethyl acetate, washed with water, dried over sodium sulfate and evaporated, firstly in a water-jet vacuum and then in a high vacuum. The semi-crystalline residue was filtered over silica gel (eluent hexane/ethyl acetate=2:1, then ethyl acetate) and recrystallized from ethyl acetate/hexane. There were obtained 19 g of benzyl 6-hydroxy-nicotinate in colourless crystals, m.p. 178–179° C.

EXAMPLE 2

980 mg of 3-hexyl-5,5-dimethyl-6,7,8,9-tetrahydro-5H-benzocycloheptene-2-carboxylic acid were placed in 5 ml of $CH_2Cl_2$ and treated with 745 mg of benzyl 6-hydroxy-nicotinate and 32 mg of 4-dimethylamino pyridine ("DMAP"). 738 mg (1 eq.) of dicyclohexylcarbodiimide were added thereto at 0° and the mixture was left to react at room temperature for 1 h. The mixture was diluted with diethyl ether, adsorbed on Merck Kieselgel 60, evaporated and the residue was chromatographed on $SiO_2$ (hexane/ethyl acetate=93/7). There were thus isolated 1.19 g of benzyl 6-(3-hexyl-5,5-dimethyl-6,7,8,9-tetrahydro-5H-benzocyclohepten-2-yl-carbonyloxy)-nicotinate as a colorless oil.

1.37 g of benzyl 6-(3-hexyl-5,5-dimethyl-6,7,8,9-tetrahydro-5H-benzocyclohepten-2-yl-carbonyloxy)-nicotinate were placed in 26 ml of ethyl acetate and hydrogenated over 137 mg of Pd/C (5%) at room temperature and under 1 atm. of $H_2$ for 4 h. The mixture was filtered over diatomaceous earth, the filtrate was evaporated to dryness and the residue was recrystallized from hexane/ethyl acetate. There were thus obtained 900 mg of 6-(3-hexyl-5,5-dimethyl-6,7,8,9-tetrahydro-5H-benzocyclohepten-2-yl-carbonyloxy)-nicotinic acid as colorless crystals of m.p. 119–120°.

Preparation of the Starting Material 3.58 g of 2-bromo-9,9-dimethyl-6,7,8,9-tetrahydro-5H-benzocycloheptene (preparation described in Eur. Pat. Application EP 410,358 A) were placed in 10 ml of piperidine under Ar. 160 mg of $((Ph)_3P)_4Pd$, 47 mg of CuI and 45 mg of $(Ph)_3P$ were added thereto in succession and then 4.8 ml (3 eq.) of 1-hexyne were added dropwise thereto at 80° within 1 h. The mixture was left to react at the same temperature for 2 h., then poured on to ice/HCl, extracted with hexane, washed twice with $H_2O$, dried over $Na_2SO_4$ and evaporated to dryness. Flash chromatography on $SiO_2$ (hexane) gave 3.25 g of 2-(hex-1-ynyl)-9,9-dimethyl-6,7,8,9-tetrahydro-5H-benzocycloheptene as a colorless oil (GC purity: 98%).

This alkyne was dissolved in 30 ml of ethy acetate and hydrogenated over 2 g of Pd/C (10%) at room temperature and under 1 atm $H_2$. Filtration over diatomaceous earth and removal of the solvent gave 3.08 g of 2-hexyl-9,9-dimethyl-6,7,8,9-tetrahydro-5H-benzocycloheptene as a colorless oil (GC purity: 98%).

This 3.08 g of 2-hexyl-9,9-dimethyl-6,7,8,9-tetrahydro-5H-benzocycloheptene were dissolved in 35 ml of $CH_2Cl_2$, treated at 0° with a spatula tip of Fe powder and then reacted with a solution of 0.67 ml of $Br_2$ (1.1 eq.) in 5 ml of $CH_2Cl_2$. After 30 min., the mixture was poured on to ice, extracted with diethyl ether, washed with bisulphite solution and NaCl soln., dried over $Na_2SO_4$ and evaporated to dryness. Flash chromatography on $SiO_2$ (hexane) gave 3.21 g of 2-bromo-3-hexyl-5,5-dimethyl-6,7,8,9-tetrahydro-5H-benzocycloheptene as a colorless oil (GC purity: 82%, moreover 2% ed., 2.6% regioisomer, 8.3% dibromo compound and further prod.).

This 3.21 g of 2-bromo-3-hexyl-5,5-dimethyl-6,7,8,9-tetrahydro-5H-benzocycloheptene were placed in 30 ml of abs. tetrahydrofuran under Ar and treated at −78° with 6.75 ml of 1.55M nBuLi (hexane) (1.1 eq.). The metal/halogen exchange was followed by gas chromatography (GC). After 40 min., a large excess of $CO_2$ gas was introduced and the cooling bath was removed. After 10 min., the mixture was poured on to ice/$NH_4Cl$ solution, extracted with diethyl ether, washed with $H_2O$, dried over $Na_2SO_4$ and the solvent was removed in a vacuum. Flash chromatography on $SiO_2$ (hexane/ethyl acetate=8/2) yielded 2.26 g of 3-hexyl-5,5-dimethyl-6,7,8,9-tetrahydro-5H-benzocycloheptene-2-carboxylic acid as white crystals of m.p. 74–75°.

EXAMPLE 3

In analogy to Example 2, starting from 5-bromo-1,1-dimethyl-indane (preparation described in Org. Prep. Proced. Int. 10, 123 (1978)) there was obtained 6-(6-hexyl-3,3-dimethyl-indan-5-yl-carbonyloxy)-nicotinic acid as white crystals of m.p. 104–105° C.

EXAMPLE 4

805 mg of (Z)-3-hex-1-enyl-5,5,8,8-tetramethyl-5,6,7,8-tetrahydro-naphthalene-2-carboxylic acid were dissolved in 8 ml of $CH_2Cl_2$ and treated with 679 mg (1 eq.) of 4-trimethylsilanyl-(E)-but-2-enyl 6-hydroxy-nicotinate and 24 mg of 4-dimethyl-aminopyridine. 581 mg (1 eq.) of dicyclohexylcarbodiimide were added thereto at 0° and the mixture was left to react at room temperature for 4 h. The precipitated urea was filtered off, the filtrate was evaporated and the crude product was purified by flash chromatography on $SiO_2$ (hexane/ethyl acetate=95:5). There were thus isolated 971 mg of 4-trimethylsilanyl-(E)-but-2-enyl 6-(3-(Z)-1-hexenyl-5,5,8,8-tetramethyl-5,6,7,8-tetrahydro-naphthalen-2-yl-carbonyloxy)-nicotinate as a colorless lacquer.

970 mg of 4-trimethylsilanyl-(E)-but-2-enyl 6-(3-(Z)-1-hexenyl-5,5,8,8-tetramethyl-5,6,7,8-tetrahydro-naphthalen-2-yl-carbonyloxy)-nicotinate were dissolved in 8 ml of $CH_2Cl_2$ and treated at room temperature with 40 mg (2 mol %) of $((Ph)3P)_4Pd$. The mixture was stirred for 4½ h. with the exclusion of oxygen, then poured into 100 ml of ethyl acetate in which 4.5 g of $SiO_2$ had been suspended and stirred for 10 min. The mixture was suction filtered, the filter material was rinsed thoroughly with ethyl acetate and the filtrate was evaporated to dryness. Three-fold recrystallization from hexane/ethyl acetate finally gave 334 mg of 6-(3-(Z)-1-hexenyl-5,5,8,8-tetramethyl-5,6,7,8-tetrahydro-naphthalen-2-yl-carbonyloxy)-nicotinic acid as white crystals of m.p. 133–135° (dec.).

The 4-trimethylsilanyl-(E)-but-2-enyl 6-hydroxy-nicotinate was prepared as follows:

1.3 g of 4-trimethylsilyl-(E)-but-2-en-1-ol (synthesis described in *J. Org. Chem.* 1984, 49, 4092), 1.08 g of 6-hydroxy-nicotinic acid and 178 mg of 4-dimethylaminopyridine were placed in succession in 30 ml of abs. dimethylformamide. 1.77 g (1.1 eq.) of dicyclohexylcarbodiimide were added thereto at 0° and the mixture was left to react at room temperature overnight. The separated urea was filtered off, the filtrate was extracted with ethyl acetate, washed twice with $H_2O$, dried over $Na_2SO_4$ and the solvent was removed under reduced pressure. Flash chromatography on $SiO_2$ (hexane/ethyl acetate=1/1) yielded 782 mg of 4-trimethylsilanyl-(E)-but-2-enyl 6-hydroxy-nicotinate as white crystals of m.p. 107–110° (dec.).

The (Z)-3-hex-1-enyl-5,5,8,8-tetramethyl-5,6,7,8-tetrahydro-naphthalen-2-yl-carboxylic acid was prepared as follows:

15 g of 5,5,8,8-tetramethyl-tetrahydro-naphthalen were dissolved in 160 ml of $CH_2Cl_2$, treated with a spatula tip of Fe powder and then reacted with a solution of 10.1 ml of $Br_2$ (2.5 eq.) in 50 ml of $CH_2Cl_2$. After ¼ h, the mixture was poured on to ice, extracted with diethyl ether, washed with bisulphite alkali and $H_2O$, dried over $Na_2SO_4$ and evaporated to dryness. Column filtration over $SiO_2$ (hexane) gave 25.3 g of 2,3-dibromo-5,5,8,8-tetramethyl-tetrahydronaphthalene as yellowish crystals of m.p. 117–120°.

10 g of 2,3-dibromo-5,5,8,8-tetramethyl-5,6,7,8-tetrahydro-naphthalene were placed in 25 ml of piperidine. 668 mg of $((Ph)_3P)_4Pd$, 211 mg of CuI and 291 mg of $(Ph)_3P$ were added thereto in succession and then 5.16 ml (1.59 eq.) of 1-hexyne dissolved in 12 ml of piperidine were added dropwise at 75–80° within 2½ h. The mixture was left to react at the same temperature for 1 h., then poured on to ice/HCl, extracted with diethyl ether, washed with $H_2O$, dried over $Na_2SO_4$ and evaporated to dryness. Flash chromatography on $SiO_2$ (hexane) gave 6.67 g of 6-bromo-7-hex-1-ynyl-1,1,4,4-tetramethyl-1,2,3,4-tetrahydronaphthalene as yellowish crystals of m.p. 59–63°.

6.67 g of 6-bromo-7-hex-1-ynyl-1,1,4,4-tetramethyl-1,2,3,4-tetrahydronaphthalene were dissolved in 270 ml of ethanol and hydrogenated at 40° and 1 atm of $H_2$ for several days in the presence of Lindlar catalyst. The reaction mixture was very resinous throughout the reaction. After 0 h., 24 h., 48 h., etc. 6.7 g of fresh catalyst were added each time; after 5 days, the mixture was filtered over diatomaceous earth and the reaction was started again. After a total of 9 days, the catalyst was again filtered off, the solvent was removed under reduced pressure and the residue was purified by flash chromatography on $SiO_2$ (hexane). There were obtained 3.72 g of product which contained 75% of (Z)-6-bromo-7-hex-1-enyl-1,1,4,4-tetramethyl-1,2,3,4-tetrahydronaphthalene according to GC.

3.72 g of (Z)-6-bromo-7-hex-1-enyl-1,1,4,4-tetramethyl-1,2,3,4-tetrahydro-naphthalene (75% pure) were placed in 25 ml of abs. tetrahydrofuran and treated at −75° with 8.25 ml of 1.55M n-BuLi (hexane) (1.2 eq.). After ½ h., a $CO_2$ stream was conducted vigorously through the solution for 30 min., with the temperature rising to −60° in spite of constant cooling. The mixture was left to warm to room temperature, poured on to ice/HCl solution, extracted with diethyl ether, washed with $H_2O$, dried over $Na_2SO_4$ and the solvent was removed in a vacuum. Two-fold flash chromatography on $SiO_2$ (hexane/ethyl acetate=85/15, then 9/1) yielded 1.06 g of (Z)-3-hex-1-enyl-5,5,8,8-tetramethyl-5,6,7,8-tetrahydro-naphthalene-2-carboxylic acid as colorless crystals.

EXAMPLE 5

In analogy to Example 1, by reacting 6-bromo-1,1,4,4-tetramethyl-7-pentyl-1,2,3,4-tetrahydronaphthalene with tert.butyl-lithium and subsequently introducing carbon dioxide gas there was prepared 5,5,8,8-tetramethyl-3-pentyl-5,6,7,8-tetrahydro-naphthalene-2-carboxylic acid (m.p. 123–124° C. hexane). Reaction of this acid with benzyl 6-hydroxy-nicotinate gave, after recrystallization from hexane, benzyl 6-(3-pentyl-5,5,8,8-tetramethyl-5,6,7,8-tetrahydro-naphthalen-2-yl-carbonyloxy)-nicotinate, m.p. 94–95° C.

Removal of the benzyl protecting group by hydrogenation with hydrogen/palladium-charcoal yielded, after recrystallization from ethyl acetate/hexane, the desired end product 6-(3-pentyl-5,5,8,8-tetramethyl-5,6,7,8-tetrahydro-naphthalen-2-yl-carbonyloxy)-nicotinic acid in white crystals, m.p. 139–141° C.

EXAMPLE 6

In analogy to Example 1, by metallating 6-bromo-7-pentoxy-1,1,4,4-tetramethyl-1,2,3,4-tetrahydro-naphthalene with tert.butyl-lithium and reacting with carbon dioxide gas there was prepared 3-pentoxy-5,5,8,8-tetramethyl-5,6,7,8-tetrahydro-naphthalene-2-carboxylic acid (m.p. 67–68° C., from hexane). Reaction of this acid with benzyl 6-hydroxy-nicotinate gave benzyl 6-(3-pentoxy-5,5,8,8-tetramethyl-5,6,7,8-tetrahydro-naphthalen-2-carbonyloxy)-nicotinate as a colorless oil. Subsequent hydrogenation yielded the desired end product 6-(3-pentoxy-5,5,8,8-tetramethyl-5,6,7,8-tetrahydro-naphthalen-2-yl-carbonyloxy)-nicotinic acid in white crystals, m.p. 132–133° C. (from diethyl ether/hexane).

EXAMPLE 7

9.3 g of (2-adamantan-1-yl-4-bromo-phenoxy)-tert-butyl-dimethylsilane were dissolved in 120 ml of absolute tetrahydro-furan and treated dropwise at −78° C. with 15.5 ml of a 1.6 molar solution of n-butyl-lithium in hexane. After stirring at −78° C. for 1.5 hours, a vigorous stream of carbon dioxide was introduced for one hour. Subsequently, the reaction mixture was firstly poured into ice-cold, saturated, aqueous ammonium chloride solution, acidified cautiously to pH 3 with cold 2N hydrochloric acid and extracted with ethyl acetate. After washing once with water, drying over sodium sulfate and evaporation there was obtained a white, crystalline mass which was recrystallized from ethyl acetate and gave 7 g of 3-adamantan-1-yl-4-(tert-butyl-dimethyl-silanyloxy)-benzoic acid. m.p. 250–252° C.

770 mg of this acid were dissolved in 50 ml of methylene chloride. After the addition of a solution of 400 mg of allyl 6-hydroxy-nicotinate in 20 ml of methylene chloride and of 244 mg of 4-dimethylaminopyridine the solution was cooled to 0° C. and treated with 450 mg of dicyclohexylcarbodi-imide. The reaction mixture was stirred at room temperature for 2 days, poured into ice-cold, aqueous ammonium chloride solution and extracted with ethyl acetate. The partially crystalline material obtained after drying and evaporation was firstly filtered over silica gel (eluent hexane/10% ethyl acetate) and subsequently purified further by medium pressure chromatography (Lobar column, eluent hexane/5% ethyl acetate) and recrystallization from hexane. There were obtained 300 mg of allyl 6-[3-adamantan-1-yl-4-(tert-butyl-dimethyl-silanyloxy)-benzoyl-oxy]-nicotinate in glistening platelets, m.p. 130–132° C.

100 mg of this ester were dissolved in 5 ml of absolute tetrahydrofuran and treated under argon with 104 mg of tetrakis-(triphenylphosphine)-palladium and 61 mg of tributyltin hydride. After stirring at room temperature for 30 min., the reaction mixture was poured on to ice/saturated ammonium chloride solution, acidified with 1N hydrochloric acid and extracted with ethyl acetate. The dark oil obtained after drying and evaporation was purified by chromatography (RP18-LiChroprep, acetonitrile) and recrystallization from ethyl acetate. There were obtained 21 mg of 6-[3-adamantan-1-yl-4-(tert-butyl-dimethyl-silanyloxy)-benzoyloxy]-nicotinic acid in colorless crystals, m.p. 188–190° C.

68 mg of this acid were dissolved in 5 ml of tertrahydro-furan and treated with 50 mg of tetrabutylammonium fluoride. After stirring at room temperature for 30 minutes, the reaction mixture was poured on to ice, acidified with 0.1N hydrochloric acid and extracted with ethyl acetate. The crystalline substance obtained after drying and evaporation of the solvent was recrystallized from acetonitril. 6-(3-Adamantan-1-yl-4-hydroxy-benzoyloxy)-nicotinic acid of m.p. 169–172° C. was obtained.

The allyl 6-hydroxy-nicotinate used as the starting material was prepared in analogy to the synthesis of benzyl 6-hydroxy-nicotinate described in Example 1 by the acid-catalyzed esterification of 6-hydroxy-nicotinic acid with allyl alcohol, m.p. 112–113° C. (from ethyl acetate/hexane).

EXAMPLE A

Hard gelatin capsules can be produced as follows:

| | Ingredients | mg/capsule |
|---|---|---|
| 1. | Spray-dried powder containing 75% compound I | 20 |
| 2. | Sodium dioctylsulphosuccinate | 0.2 |
| 3. | Sodium carboxymethylcellulose | 4.8 |
| 4. | Microcrystalline cellulose | 86.0 |

-continued

| | Ingredients | mg/capsule |
|---|---|---|
| 5. | Talc | 8.0 |
| 6. | Magnesium stearate | 1.0 |
| | Total | 120 |

The spray-dried powder, which is based on the active ingredient, gelatin and microcrystalline cellulose and which has an average active ingredient particle size of $<1\mu$ (measured by autocorrelation spectroscopy) is moistened with an aqueous solution of sodium carboxymethylcellulose and sodium dioctylsulphosuccinate and kneaded. The resulting mass is granulated, dried and sieved, and the granulate obtained is mixed with microcrystalline cellulose, talc and magnesium stearate. The mixture is filled into size 0 capsules.

EXAMPLE B

Tablets can be produced as follows:

| | Ingredients | mg/tablet |
|---|---|---|
| 1. | Compound I as a finely milled powder | 20 |
| 2. | Powd. lactose | 100 |
| 3. | White corn starch | 60 |
| 4. | Povidone K30 | 8 |
| 5. | White corn starch | 112 |
| 6. | Talc | 16 |
| 7. | Magnesium stearate | 4 |
| | Total | 320 |

The finely milled substance is mixed with lactose and a portion of the corn starch. The mixture is moistened with an aqueous solution of Povidone K30 and kneaded, and the resulting mass is granulated, dried and sieved. The granulate is mixed with the remaining corn starch, talc and magnesium stearate and pressed to tablets of suitable size.

EXAMPLE C

Soft gelatin capsules can be produced as follows:

| | Ingredients | mg/capsule |
|---|---|---|
| 1. | Compound I | 5 |
| 2. | Triglyceride | 450 |
| | Total | 455 |

1 g of compound I is dissolved in 90 g of medium chain triglyceride with stirring, inert gasification and protection from light. This solution is processed as a capsule fill mass to soft gelatin capsules containing 5 mg of active ingredient.

EXAMPLE D

A lotion can be prepared as follows:

| | Ingredients | |
|---|---|---|
| 1. | Compound I, finely milled | 1.0 g |
| 2. | Carbopol 934 | 0.6g |
| 3. | Sodium hydroxide | q.s. ad pH 6 |

-continued

| | Ingredients | |
|---|---|---|
| 4. | Ethanol, 94% | 50.0 g |
| 5. | Demineralized water | ad 100.0 g |

The active ingredient is incorporated into the 94% ethanol/water mixture with protection from light. Carbopol 934 is stirred in until gelling is complete and the pH value is adjusted with sodium hydroxide.

EXAMPLE E

A cream can be produced in a known manner from the ingredients listed hereinafter:

| | Wt. % |
|---|---|
| Compound of formula I | 0.1–5 |
| Cetyl alcohol | 5.25–8.75 |
| Arlacel 165 (glyceryl/PEG 100 stearate) | 3.75–6.25 |
| Myglyol 818 (caprylic/capric/linoleic acid) | 11.25–18.75 |
| Sorbitol solution | 3.75–6.25 |
| Ethylene diamine tetraacetate (EDTA) Na$_2$ | 0.075–0.125 |
| Carbopol 934P (carbomer 934P) | 0.15–0.25 |
| Butylated hydroxyanisole | 0.0375–0.0625 |
| Methylparaben | 0.135–0.225 |
| Propylparaben | 0.0375–0.0625 |
| NaOH (10% solution) | 0.15–0.25 |
| Water q.s. | 100.00 |

EXAMPLE F

A gel can be produced in a known manner from the ingredients listed hereinafter:

| | Wt. % |
|---|---|
| Compound of formula I | 0.1–5 |
| Pluronic L 101 (poloxamer 331) | 10.00 |
| Aerosil 200 (silicion dioxide) | 8.00 |
| PCL liquid (fatty acid ester) | 15.00 |
| Cetiol V (decyl oleate) | 20.00 |
| Neobee oil (medium chain length triglyceride) | 15.00 |
| Euhanol G (octyldodecanol), q.s. | 100.00 |

The physical properties of the preparations can be altered by varying the ratio between the adjuvants of Examples E and F.

We claim:

1. A method of promoting wound healing, comprising topically administering to a host in need of such healing a compound of the formula

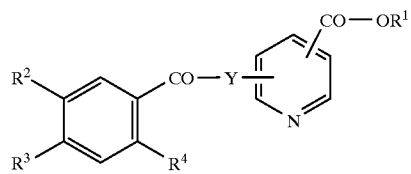

wherein
$R^1$ is hydrogen or $C_{1-6}$-alkyl;
$R^2$ is $C_{1-6}$-alkyl or adamantyl;
$R^3$ is $C_{1-6}$-alkyl or hydroxy; or
$R^2$ and $R^3$ taken together are —$(CR^6R^7)_n$—;
$R^4$ is $C_{2-8}$-alkyl, $C_{2-8}$-alkenyl, $C_{2-8}$-alkynyl, —$OCH_2R^5$ or $C_2$ alkanoyl; and hydrogen when
$R^3$ is hydroxy;
$R^5$ is $C_{1-6}$-alkyl, $C_{2-6}$-alkenyl or $C_{2-6}$-alkynyl;
$R^6$ and $R^7$ are hydrogen or $C_{1-6}$-alkyl;
Y is oxygen or sulphur; and
n is 3,4 or 5,
or a pharmaceutically usable salt of a carboxylic acid of formula I.

2. A method of treating dermatological disorders which are accompanied by epithelial lesions comprising topically administering to a host in need of such treatment a compound of the formula

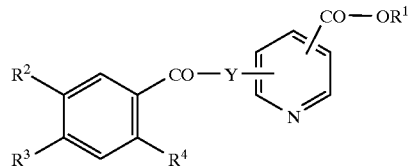

wherein
$R^1$ is hydrogen or $C_{1-6}$-alkyl;
$R^2$ is $C_{1-6}$-alkyl or adamantyl;
$R^3$ is $C_{1-6}$-alkyl or hydroxy; or
$R^2$ and $R^3$ taken together are —$(CR^6R^7)_n$—;
$R^4$ is $C_{2-8}$-alkyl, $C_{2-8}$-alkenyl, $C_{2-8}$-alkynyl, —$OCH_2R^5$ or $C_{2-8}$-alkanoyl; and hydrogen when
$R^3$ is hydroxy;
$R^5$ is $C_{1-6}$-alkyl, $C_{2-6}$-alkenyl or $C_{2-6}$-alkynyl;
$R^6$ and $R^7$ are hydrogen or $C_{1-6}$-alkyl;
Y is oxygen or sulphur; and
n is 3,4 or 5,
or a pharmaceutically usable salt of a carboxylic acid of formula I.

* * * * *

UNITED STATES PATENT AND TRADEMARK OFFICE
CERTIFICATE OF CORRECTION

PATENT NO. : 5,958,956
DATED : September 28, 1999
INVENTOR(S) : Klaus, et al.

It is certified that error appears in the above-identified patent and that said Letters Patent is hereby corrected as shown below:

Claim 1, Column 12, line 18: "$C_2$ alkanoyl;" should read --- $C_{2-8}$-alkanoyl; ---.

Signed and Sealed this

Ninth Day of May, 2000

Attest:

Q. TODD DICKINSON

*Attesting Officer*     *Director of Patents and Trademarks*